United States Patent [19]

Noda et al.

[11] Patent Number: 5,442,122

[45] Date of Patent: Aug. 15, 1995

[54] DIBENZOSUBERYL AND DIBENZOSUBERENYL DERIVATIVES

[75] Inventors: Masaki Noda, Ohmihachiman; Kiyoshi Nokihara, Kyoto, both of Japan

[73] Assignee: Shimadzu Corporation, Kyoto, Japan

[21] Appl. No.: 145,101

[22] Filed: Nov. 3, 1993

[30] Foreign Application Priority Data

Nov. 9, 1992 [JP] Japan ................... 4-324759

[51] Int. Cl.$^6$ .......................................... C07C 211/00
[52] U.S. Cl. .................................. 564/426; 564/427; 525/54.11; 530/816
[58] Field of Search ...................... 564/308, 426, 427; 525/54.11; 530/816

[56] References Cited

U.S. PATENT DOCUMENTS 3,052,721  9/1962  Bernstein et al. ............ 564/427
3,489,836  1/1970  Waring ........................ 564/427

FOREIGN PATENT DOCUMENTS 0473411  3/1992  European Pat. Off. .

OTHER PUBLICATIONS

J. Pless, Helvetica Chimica Acta, vol. 59, Fasc. 2 (1976), p. 499 (1976).

*Primary Examiner*—Nathan M. Nutter
*Attorney, Agent, or Firm*—Birch, Stewart, Kolasch & Birch

[57] ABSTRACT

The present invention is directed to a compound represented by the following formula (I),

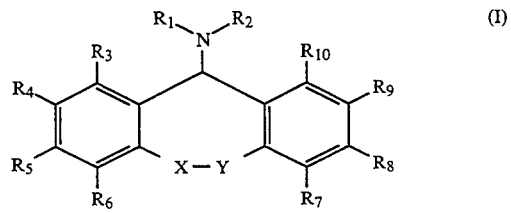

and a linker for peptide synthesis using the above compound. When the linker of the present invention is used for the solid-phase peptide synthesis, it is possible to synthesize those peptides which are sensitive to acid and difficult to synthesize by conventional methods. Also, side reactions can be prevented, and the desired product is produced at a high purity because cleavage can be achieved under milder conditions or in shorter times. In other words, efficient peptide synthesis is possible.

7 Claims, 1 Drawing Sheet

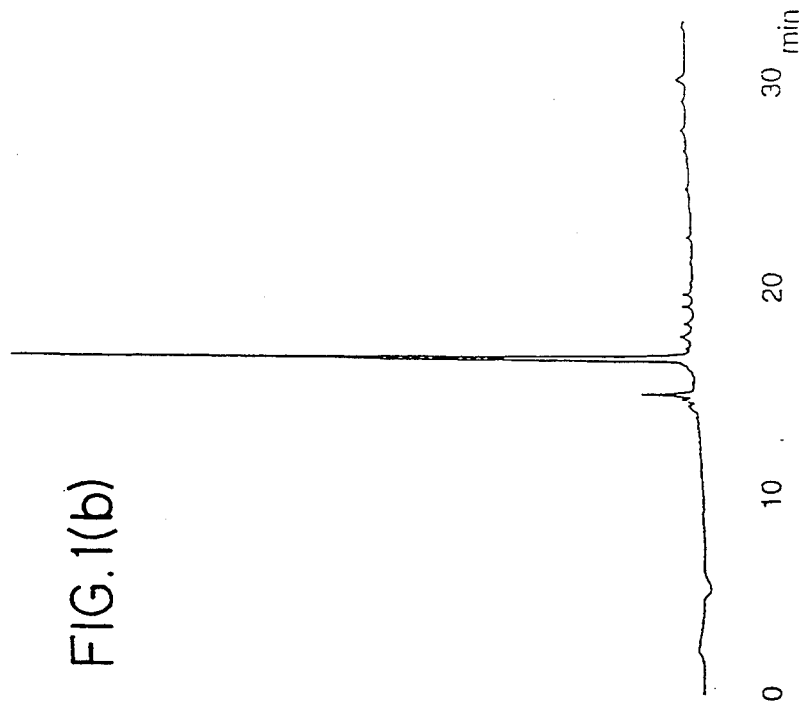
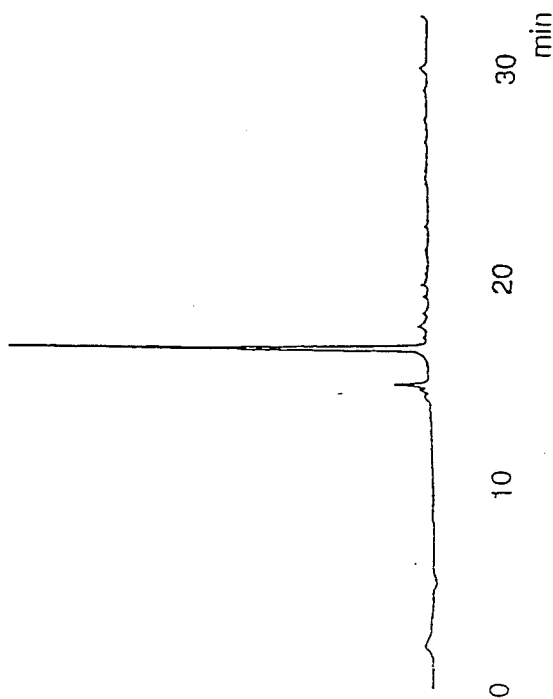

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHITICAL: NO ( i v ) ANTI-SENSE: NO ( x i ) SEQUENCE DESCRIPTION: SEQ ID NO:1:

```
Phe   Val   Gly   Leu   Met
1                       5
```

( 2 ) INFORMATION FOR SEQ ID NO:2:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHITICAL: NO ( i v ) ANTI-SENSE: NO ( x i ) SEQUENCE DESCRIPTION: SEQ ID NO:2:

```
His   Ser   Asp   Gly   Thr   Phe   Thr   Ser   Glu   Leu   Ser   Arg   Leu   Arg   Glu   Gly
1                   5                             10                            15
Ala   Arg   Leu   Gln   Arg   Leu   Leu   Gln   Gly   Leu   Val
                  20                            25
```

DIBENZOSUBERYL AND DIBENZOSUBERENYL DERIVATIVES

BACKGROUND OF THE INVENTION

1. Field of the Invention

The present invention relates to novel compounds for linkers. More particularly, the compounds of the present invention are directed to linkers for peptide synthesis which are useful in the study of peptide chemistry and production of peptide pharmaceuticals.

2. Discussion of the Related Art

Peptide synthesis is very important in peptide research. This is because many peptide amides are bioactive substances, e.g., neurotransmitter hormones, gastrointestinal hormones, and because it is generally difficult to produce them by genetic engineering. Solid-phase peptide synthesis (hereinafter simply abbreviated as "SPPS") was first achieved by Merefield using Boc-amino acid.

In recent years, there have been proposed various methods for efficiently synthesizing peptides at a high purity using an automated peptide synthesizer based on SPPS. Among them, the method using α-fluorenylmethyloxycarbonyl(Fmoc)-amino acid has recently formed the mainstream of SPPS, because it allows peptide synthesis under mild conditions. In peptide synthesis using the peptide synthesizer, specific cleavage should be carried out between the resin, i.e., solid phase, and the chain to be elongated such as a peptide chain, using an appropriate linker resin, i.e., support. Various linker resins for synthesizing peptide amides have been reported. Examples of the linker resins presently used include those represented by the following formulas:

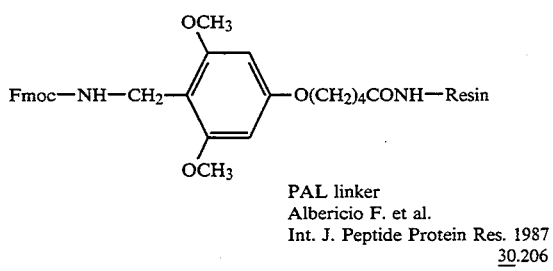

PAL linker
Albericio F. et al.
Int. J. Peptide Protein Res. 1987 30.206

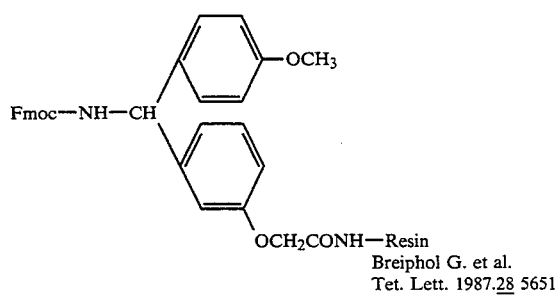

Breiphol G. et al.
Tet. Lett. 1987.28 5651

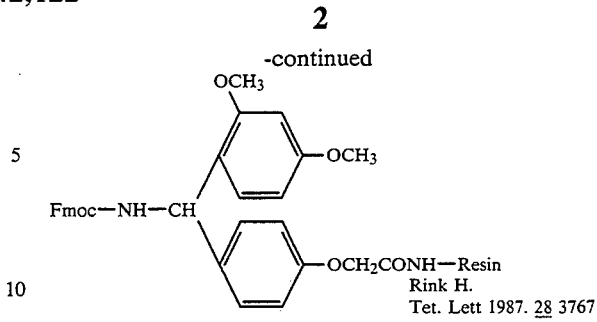

Rink H.
Tet. Lett 1987. 28 3767

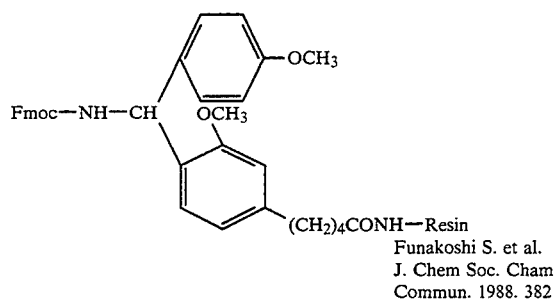

Funakoshi S. et al.
J. Chem Soc. Cham Commun. 1988. 382

Also, the following tricyclic linkers have recently been reported.

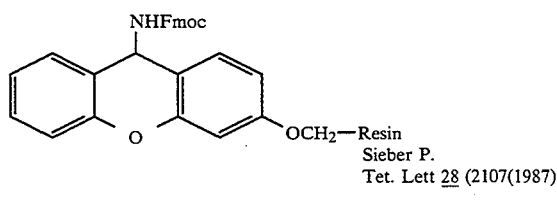

Sieber P.
Tet. Lett 28 (2107(1987)

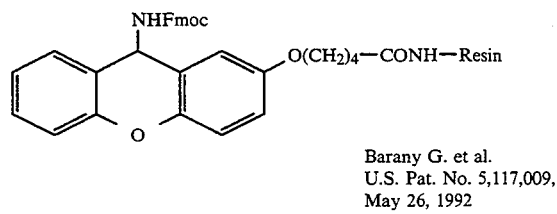

Barany G. et al.
U.S. Pat. No. 5,117,009, May 26, 1992

However, the linkers mentioned above do not show good reactivity under even milder conditions.

SUMMARY OF THE INVENTION

An object of the present invention is to provide a novel compound used as linkers for stably producing peptides under even milder conditions.

The compound of the present invention is represented by the following formula (I):

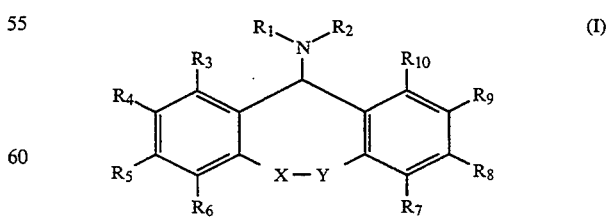

wherein $R_1$ represents a hydrogen atom, an amino acid residue protected by an amino-protecting group which is removable in the presence of a base, or an α-fluorenylmethyloxycarbonyl group; $R_2$ represents a hydrogen atom or an alkyl group having 1 to 4 carbon atoms; one substituent selected from the group consisting of $R_3$, $R_4$, $R_5$, $R_6$, $R_7$, $R_8$, $R_9$ and $R_{10}$ represents —O—$(CH_2)_n$—COOH, wherein n is an integer of 1 to 6, and all of the remaining substituents independently represent a hydrogen atom, an alkyl group having 1 to 4 carbon atoms, or an alkoxy group having 1 to 4 carbon atoms; and —X—Y— represents a —C—C— bond or a —C=C— bond.

BRIEF DESCRIPTION OF THE DRAWING

The present invention will become more fully understood from the detailed description given hereinbelow and the accompanying drawing which is given by way of illustration only, and thus, is not limitative of the present invention, and wherein:

FIG. 1(a) shows the reverse phase HPLC pattern of a crude product of a synthetic human secretin obtained using a TentaGelS-CHA linker (i.e, a TentaGelS 5-Fmoc-aminodibenzosuberyl linker); Main Peak: M+H 3039.8 (M=3038.7); Column: SynProPep RPC18 (4.6×150 mm); Eluent 0.01 N HCl/$CH_3$CN=80/20−50/50 (30 min); Flow Rate: 1.0 mL/min, Absorbance: 210 nm.

FIG. 1(b) shows the reverse phase HPLC pattern of a crude product of a synthetic human secretin obtained using a TentaGelS-CHE linker (i.e., a TentaGelS 5-Fmoc-aminodibenzosuberenyl linker); Main Peak: M+H 3039.8 (M=3038.7); Column: SynProPep RPC18 (4.6×150 mm); Eluent 0.01 N HCl/$CH_3$CN=80/20−50/50 (30 min); Flow Rate: 1.0 mL/min, Absorbance: 210 nm.

DETAILED DESCRIPTION OF THE INVENTION

The present inventors have newly synthesized peptide amide linkers incorporating a dibenzosuberyl group and a dibenzosuberenyl group, respectively by taking note of the fact that the dibenzosuberyl group is used to protect amino acids [J. Pless, Helv. Chemi., Acta 59, 499 (1976)]. Such linkers of the present invention have two benzene rings fixed essentially on the same plane. Therefore, at the time of peptide synthesis, it is presumed that cations produced in cleavage of peptide from the solid phase are likely to be stabilized by the two benzene rings of the linker, so that peptide synthesis can be achieved under mild conditions.

Specifically, the compound of the present invention has the following formula:

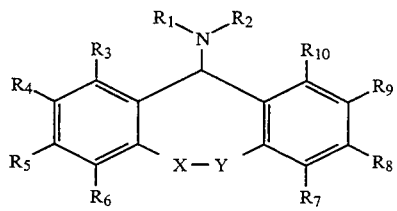

(I)

In the compound of the present invention, $R_1$ can be a hydrogen atom, an amino acid residue protected by an amino-protecting group such as an α-fluorenylmethyloxycarbonyl group which is removable in the presence of a base, or an α-fluorenylmethyloxycarbonyl group. Although $R_2$ can either be a hydrogen atom or be an alkyl group having 1 to 4 carbon atoms, it is preferred to be a hydrogen atom when $R_1$ is an amino acid residue protected by an α-fluorenylmethyloxycarbonyl group, or an α-fluorenylmethyloxycarbonyl group.

Any one of $R_3$, $R_4$, $R_5$, $R_6$, $R_7$, $R_8$, $R_9$ and $R_{10}$ represent —O—$(CH_2)_n$—COOH, wherein n is an integer of 1 to 6, and all of the remaining substituents represent a hydrogen atom, an alkyl group having 1 to 4 carbon atoms, or an alkoxy group having 1 to 4 carbon atoms. The preferred embodiment is the one where one of these substituents is —O—$(CH_2)_4$—COOH and 4 or more of the remaining substituents are hydrogen atoms. —X—Y— can either be a —C—C— bond or be a —C=C— bond. The compounds of the present invention are exemplified by 5-(5-Fmoc-amino-10,11-dihydrodibenzo-[a,d]cyclohepten-2-yl)oxyvalerianic acid (Compound 7) and by 5-(5-Fmoc-aminodibenzo[a,d]cyclohepten-2-yl)oxyvalerianic acid (Compound 12).

The compounds of the present invention can be synthesized by conventional methods. For example, the following compound 7 in Route A and compound 12 in Route B are synthesized and then introduced them into the TENTAGEL S™ resin (polystyrene-polyethyleneglycol graft copolymers). The cleavage reaction rates of these valine-coupled linker-resin compounds in $CF_3COOH/CH_2Cl_2$ solution are determined. It was found that the linker (compound 7)-resin shows about 4 times easier cleavage than that of the PAL ™ linker (5-[4-(9-Fluorenylmethoxycarbonyl) aminomethyl-3,5-dimethoxyphenoxy]-valeric acid manufactured by Millipore Corporation) which has been known to be cleaved most easily, and the linker (compound 12)-resin shows a still more easier cleavage. Therefore, these linkers permit peptide synthesis under milder conditions than the conventional conditions, making it most suitable for the synthesis of acid-sensitive peptides and protected peptides.

Also, in certain kinds of amino acids, cleavage is unlikely to take place when a conventional linker-resin is used, because the linker cation produced upon cleavage undergoes a side reaction, thereby giving the peptide with poor yield. According to a recent report of peptide synthesis, it has been reported that the PAL ™ linker undergoes a side reaction upon cleavage.

As described above, the novel compounds of the present invention are useful as linkers for peptide amide synthesis because they produce peptides under milder conditions as stated above.

Accordingly, when the linker of the present invention is used for the solid-phase peptide synthesis, it is possible to synthesize those peptides which are sensitive to acid and difficult to synthesize by conventional methods. Also, side reactions can be prevented, and the desired product is produced at a high purity because cleavage can be achieved under milder conditions or in shorter times. In other words, efficient peptide synthesis is possible.

For these reasons, the linkers of the present invention allow to stably synthesize peptide amides possessing their important bioactivities, so that they can be widely used in the fields of peptide chemistry and pharmaceutical production. The linkers of the present invention can also be used in the process for specific cleavage between a solid support and a linear compound having a functional amide group at its C terminus, in the chemical synthesis of the linear compound on the solid support.

EXAMPLES

The present invention is hereinafter described in further detail by means of the following working examples, but the present invention is not limited by these examples.

Example 1

Synthesis of 5-Fmoc-Aminodibenzosuberyl Linker (Compound 7)

Route A

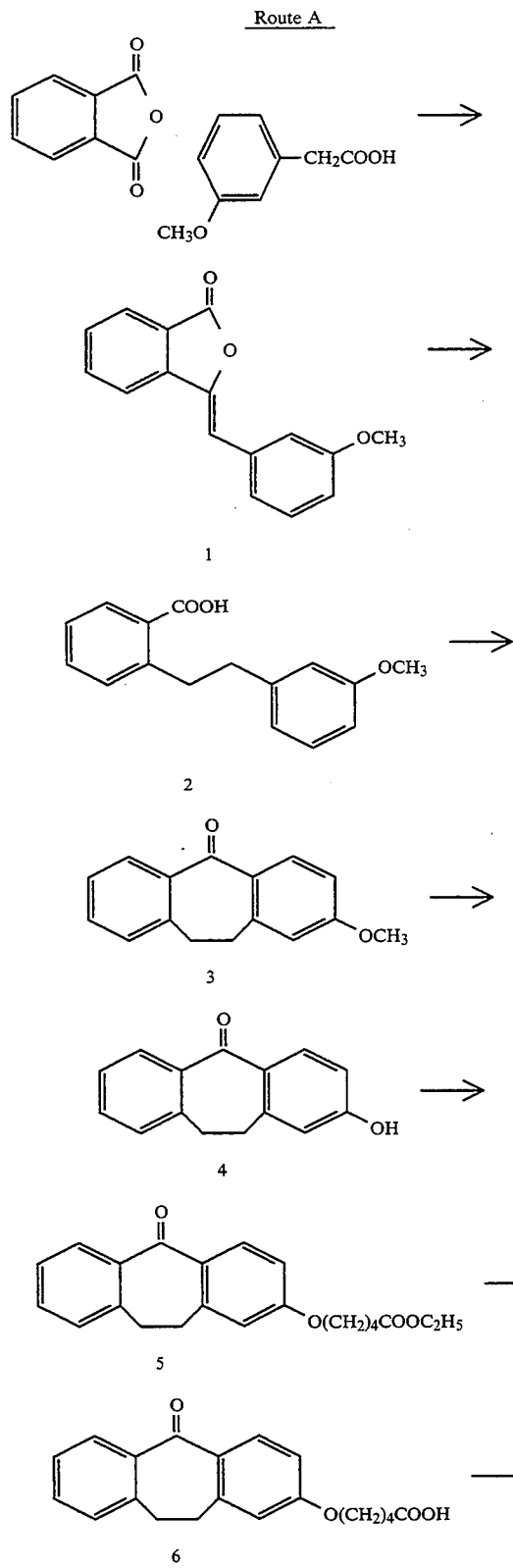

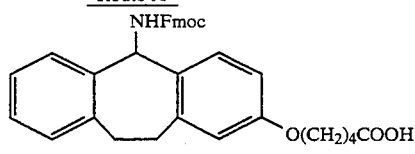

2-Methoxybenzylidene Phthalic Anhydride (Compound 1)

44.44 g (0.3 mol) of phthalic anhydride, 50 g (0.3 mol) of 3-methoxyphenylacetic acid and 0.82 g (0.04 equivalents (hereinafter abbreviated as "eq.")) of sodium acetate are placed in a 300 ml three-necked flask and stirred at a reaction temperature of 230° to 245° C. for 6 hours. The resulting water is distilled off with a condenser attached to the flask. After cooling, the residue is recrystallized from ethanol to give 58.324 g (yield 77%) of prismatic crystals having a melting point of 222° to 223° C.

| Elemental Analysis | | |
| --- | --- | --- |
| | C | H |
| Theoretical ($C_{16}H_{12}O_3$) | 76.18 | 4.80 |
| Found | 76.10 | 4.57 |

NMR (CDCl$_3$) δ(ppm): 3.33 (3H, S, OCH$_3$), 6.41 (1H, S, olefin H), 6.89 (1H, dd, J=9.6 Hz, J=2.8 Hz, benzene ring H ), 7.30–7.98 (7H, m, benzene ring H )

2-(2'-Methoxyphenethyl)benzoic Acid (Compound 2)

10 g (0.0397 mol) of 2-methoxybenzylidene phthalic anhydride (compound 1) is placed in a 500 ml autoclave. 230 ml of ethanol, 4.02 g (1 eq.) of triethylamine and 20 g of Raney nickel freshly prepared from 40 g of 50% Raney nickel alloy by a conventional method are added. The reaction mixture is stirred under an H$_2$ pressure of 4 kg/cm$^2$ at room temperature for 2 days. After the catalyst is filtered off and washed with ethanol, the filtrate is evaporated. The resulting crude crystals are recrystallized from ethyl acetate-hexane to give 6.548 g (yield 64%) of colorless acicular crystals having a melting point of 118° to 119° C.

| Elemental Analysis | | |
| --- | --- | --- |
| | C | H |
| Theoretical ($C_{16}H_{16}O_3$) | 76.10 | 4.80 |
| Found | 76.10 | 4.57 |

NMR (CDCl$_3$) δ(ppm): 2.95 (2H, m, methylene —CH$_2$—), 3.33 (2H, m, methylene —CH$_2$—), 3.78 (3H, S, OCH$_3$), 6.72–6.86 (3H, m, benzene ring H), 7.16–7.52 (4H, m, benzene ring H), 8.08 (1H, dd, J=1.4 Hz, J=9.1 Hz, benzene ring H)

2-Methoxy-10,11-dihydro-dibenzo[a,d]cyclohepten-5-one (Compound 3); (2-Methoxydibenzosuberone)

13.0 g (0.051 mol) of 2-(2'-methoxyphenethyl)benzoic acid (compound 2) is added to PPA (polyphosphoric acid, prepared by stirring 62.5 g of P$_2$O$_5$ and 40.3 ml of 85% phosphoric acid at 90° to 95° C. for 1 hour), followed by thorough stirring at room temperature and then stirring at 145° to 150° C. in N$_2$ atmosphere for 2 hours. This mixture is poured into a large amount of ice water to decompose the PPA, and then the resulting mixture is extracted with three portions of ethyl acetate.

The extract is washed with a saturated aqueous solution of NaHCO$_3$ and then with saturated saline. After the washed extract is dried over anhydrous MgSO$_4$, the solvent is evaporated, and the residue is recrystallized from ethyl acetate-hexane to give 10.641 g (yield 88%) of colorless crystals having a melting point of 72° to 73° C.

| Elemental Analysis | | |
| --- | --- | --- |
| | C | H |
| Theoretical (C$_{16}$H$_{14}$O$_2$) | 80.65 | 5.92 |
| Found | 80.93 | 5.88 |

NMR (CDCl$_3$) δ(ppm): 3.18 (4H, S, ethylene —CH$_2$CH$_2$—), 3.86 (3H, S, OCH$_3$), 6.71 (1H, d, J=3.2 Hz, benzene ring C$_1$-H), 6.86 (1H, dd, J=2.8 Hz, J=10.5 Hz, benzene ring C$_3$—H), 7.18–7.45 (3H, m, benzene ring C$_7$—H, C$_8$—H, C$_9$—H), 8.17 (1H, d, J=10.2 Hz, benzene ring C$_6$—H)

2-Hydroxy-10,11-dihydrodibenzo[a,d]cyclohepten-5-one (Compound 4); (2-Hydroxydibenzosuberone).

7.0 g (0.0294 mol) of 2-methoxydibenzosuberone (compound 3) is dissolved in 100 ml of benzene. After 8.628 g (2.2 eq.) of anhydrous AlCl$_3$ is added, the mixture is refluxed in N$_2$ atmosphere while stirring for 2 hours. After cooling, the reaction mixture is poured into ice and water, and then extracted with ethyl acetate. The extract is washed with saturated saline and dried over anhydrous MgSO$_4$, after which the solvent is evaporated, to give a yellow solid, which in turn is purified by silica gel column chromatography (developing solvent: ethyl acetate-hexane=1:3) to give 6.285 g (yield 95%) of a product (compound 4), which is recrystallized from ethyl acetate-hexane to give colorless plate-like crystals (melting point: 139° to 140° C.).

| Elemental Analysis | | |
| --- | --- | --- |
| | C | H |
| Theoretical (C$_{15}$H$_{12}$O$_2$) | 80.33 | 5.40 |
| Found | 80.17 | 5.56 |

NMR (CDCl$_3$) δ(ppm): 3.15 (4H, S, ethylene —CH$_2$CH$_2$—), 6.31 (1H, S', —OH), 6.68 (1H, d, J=2.8 Hz, benzene ring C$_1$—H), 6.80 (1H, dd, J=2.8 Hz, J=10.2 Hz, benzene ring C$_3$—H), 7.18–7.46 (3H, m, benzene ring C$_7$—H, C$_8$-H, C$_9$-H), 8.0 (1H, dd, J=1.8 Hz, benzene ring C$_4$—H), 8.13 (1H, d, J=10.2 Hz, benzene ring C$_5$—H)

Ethyl-5-(10, 11-dihydrodibenzo[a,d]cyclohepten-5-one-2-yl)oxyvalerate (Compound 5)

5.785 g (0.025 mol) of 2-hydroxydibenzosuberone (compound 4) is dissolved in 35 ml of DMF. After 1.136 g (1.1 eq.) of NaH (60%) is added, the mixture is stirred at room temperature in N$_2$ atmosphere. 5.395 g (1 eq.) of ethyl-5-bromovalerate is added dropwise to a reaction mixture cooled to 0° C., and the resulting mixture is stirred overnight at room temperature. The reaction mixture is poured into ice and water, and then neutralized with dilute hydrochloric acid. The resulting mixture is extracted with ethyl acetate. The extract is washed with saturated saline and dried over anhydrous MgSO$_4$, after which the solvent is evaporated. The oily product is purified by silica gel column chromatography (developing solvent: ethyl acetate-hexane, gradient ratio=1:7 to 1:3) to give 8.599 g (yield 95%) of a product (compound 5), which is recrystallized from ethyl acetate-hexane to give colorless crystals (melting point: 55° to 56° C.).

| Elemental Analysis | | |
| --- | --- | --- |
| | C | H |
| Theoretical (C$_{22}$H$_{24}$O$_4$) | 74.98 | 6.86 |
| Found | 74.89 | 6.77 |

NMR (CDCl$_3$) δ(ppm): 1.26 (3H, t, J=8.4 Hz, —CH$_3$), 1.8–1.9 (4H, m, ethylene —CH$_2$CH$_2$—), 2.39 (2H, t, J=8.0 Hz, methylene —CH$_2$—O—), 3.17 (4H, S, ethylene —CH$_2$CH$_2$—, C$_{10}$-H, C$_{11}$-H), 4.04 (2H, t, J=7.0 Hz, methylene —CH$_2$—COOEt), 4.14 (2H, q, J=8.4 Hz, methylene ), 6.69 (1H, d, J=3.2 Hz, benzene ring C$_1$—H), 6.84 (1H, dd, J=2.8 Hz, J=10.5 Hz, benzene ring C$_3$—H), 7.18–7.45 (3H, m, benzene ring C$_7$-H, C$_8$-H, C$_9$-H), 8.02 (1H, dd, J=1.8 Hz, benzene ring C$_4$-H), 8.16 (1H, d, J=10.0 Hz, benzene ring C$_6$—H)

5-(10,11-Dihydrodibenzo[a,d]cyclohepten-5-one-2-yl)oxyvalerianic Acid (Compound 6)

2.0 g (5.68 mmol) of ethyl-5-(10,11-dihydrodibenzo-[a,d]cyclohepten-5-one-2-yl)oxyvalerate (compound 5) is dissolved in 20 ml of dioxane. 10 ml of 2N NaOH solution is added to the solution, and the reaction mixture is stirred overnight at room temperature. The resulting mixture is acidified with dilute hydrochloric acid, and the solvent is evaporated under a reduced pressure. Water is added to the residue, and the mixture is extracted with ethyl acetate. The extract is washed with saturated saline, and dried over anhydrous MgSO$_4$, after which the solvent is evaporated to give 1.814 g (yield 98%) of the product (compound 6) which is plate-like colorless crystals (melting point: 121° to 122° C., obtained by recrystallization from ethyl acetate-hexane).

| Elemental Analysis | | |
| --- | --- | --- |
| | C | H |
| Theoretical (C$_{20}$H$_{20}$O$_4$) | 74.05 | 6.22 |
| Found | 73.93 | 6.12 |

NMR (CDCl$_3$) δ(ppm): 1.58–1.59 (4H, m, ethylene —CH$_2$CH$_2$—), 2.46 (2H, t, J=7.7 Hz, methylene —OCH$_2$), 3.17 (4H, S, ethylene —CH$_2$CH$_2$—, C$_{10}$-H, C$_{11}$-H), 4.05 (2H, t, J=20 Hz, methylene —CH$_2$—COOH), 6.7 (1H, d, J=3.2 Hz, benzene ring C$_1$—H), 6.84 (1H, dd, J=3.2 Hz, benzene ring C$_3$-H, 7.2–7.46 (3H, m, benzene ring C$_7$—H, C$_8$-H, C$_9$-H), 8.02 (1H, dd, J=1.4 Hz, J=9.1 Hz, benzene ring C$_6$—H)

5-(5-Fmoc-amino-10,11-dihydrodibenzo[a,d]cyclohepten-2-yl)oxyvalerianic Acid (Compound 7); (5-Fmoc-aminodibenzosuberyl Linker)

1.0 g (3.086 mmol) of 5-(10,11-dihydrodibenzo[a,d]-cyclohepten-5-one-2-yl)oxyvalerianic acid (compound 6) is dissolved in 50 ml of isopropyl alcohol. 0.313 g (1 eq.) of triethylamine and 0.584 g (5 eq.) of NaBH$_4$ are added to the above mixture, and the resulting mixture is stirred at 70° C. for 2 hours. The solvent is evaporated under a reduced pressure, and the residue is dissolved in water. The mixture is acidified (pH=4.0) with dilute hydrochloric acid, and the resulting mixture is extracted with ethyl acetate. The extract is washed with saturated saline, and dried over anhydrous MgSO$_4$, after which the solvent is evaporated. 1.106 g (1.5 eq.) of Fmoc-NH$_2$ is added to the obtained product having a hydroxyl group, and 40 ml of acetic acid is further added thereto, and the resulting mixture is thoroughly mixed. A catalytic amount of p-toluene sulfonic acid is added to the resulting mixture, and the mixture is stirred at room temperature for 1 hour. Crystals precipitated by adding water are filtrated, washed with water and dried. The crude product is purified by silica gel column chromatography (developing solvent: ethyl acetate-hexane=1:1, followed by ethyl acetate (5% methanol)) to give 1.377 g (yield 82%) of a product (compound 7) which is colorless crystals (melting point: 207° to 209° C., obtained by recrystallization from methanol).

| Elemental Analysis | | | |
|---|---|---|---|
| | C | H | N |
| Theoretical ($C_{35}H_{33}O_5N$) | 76.76 | 6.07 | 2.56 |
| Found | 76.14 | 5.93 | 2.74 |

NMR (DMSO-$d_6$) δ(ppm): 1.6–1.8 (4H, m, ethylene —CH$_2$CH$_2$—), 2.27 (2H, t, J=7.7 Hz, methylene —OCH$_2$—), 3.0–3.3 (4H, m, ethylene —CH$_2$CH$_2$—, C$_{10}$-H, C$_{11}$-H), 3.92 (2H, t, J=7.0 Hz, methylene —CH$_2$—COOH), 4.25 (3H, broad S, methylene, methine —COOCH$_2$CH=) 6.03 (1H, d, J=9.1 Hz, methylene C$_5$-H), 6.72 (2H, broad S, aromatic H), 7.15–7.90 (13H, m, aromatic H), 8.53 (1H, d, J=9.1 Hz, NH), 12.0 (1H, S, —COOH)

Example 2

Synthesis of 5 -Fmoc-aminodibenzosuberenyl Linker (Compound 12)

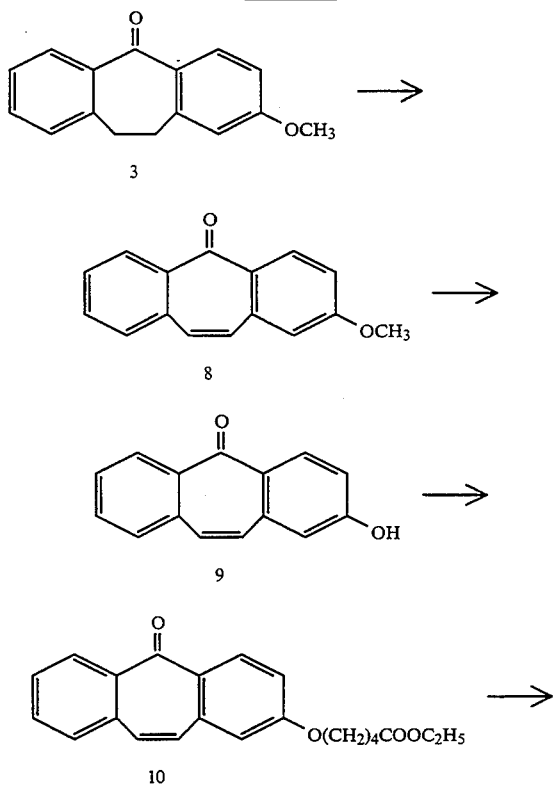

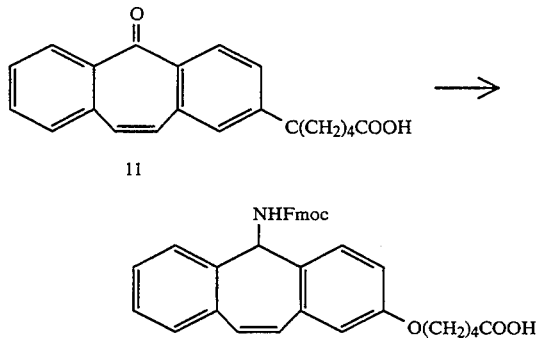

2-Methoxydibenzo[a,d]cyclohepten-5-one (Compound 8); (2-Methoxydibenzosuberenone)

6.0 g (0.025 mol) of 2-methoxydibenzosuberone (compound 3) is dissolved in 200 ml of CCl$_4$, and 4.487 g (1 eq.) of NBS is added thereto. The mixture is heated and refluxed for 16 hours. After cooling, insoluble substances are filtered off, and the solution is evaporated. The resulting oily residue is dissolved in 100 ml of triethylamine, and the resulting mixture is refluxed overnight. The solution is evaporated, and ethyl acetate and H$_2$O are added to the residue. The ethyl acetate solution is separated, and the aqueous layer is extracted from ethyl acetate. The extract is washed with dilute hydrochloric acid and then with saturated saline. The washed extract is dried over anhydrous MgSO$_4$, and the solvent is evaporated to yield a crude product. The crude product is recrystallized from ethyl acetate-hexane to give 4.115 g (yield 69%) of a product (compound 8) which is colorless acicular crystals (melting point: 75° to 76° C.).

| Elemental Analysis | | |
|---|---|---|
| | C | H |
| Theoretical ($C_{16}H_{12}O_2$) | 81.33 | 5.12 |
| Found | 81.44 | 4.98 |

NMR (CDCl3) δ(ppm): 3.92 (3H, S, OCH$_3$), 6.97 (1H, d, J=2.8 Hz, benzene ring C$_1$—H), 6.98 (1H, d, J=14 Hz, C$_{11}$-H), 7.05 (1H, d, J=14 Hz, C$_{10}$-H), 7.1 (1H, dd, J=3.2 Hz, J=10 Hz, benzene ring C$_3$—H), 7.5–7.65 (3H, m, benzene ring C$_7$-H, C$_8$-H, C$_9$-H), 8.26 (1H, d, J=10.2 Hz, benzene ring C$_4$-H), 8.28 (1H, dd, J=2.5 Hz, J=9.1 Hz, benzene ring C$_6$—H)

2-Hydroxydibenzo[a,d]cyclohepten-5-one (Compound 9); (2-hydroxydibenzosuberenone)

1.0 g of (424 mmol) of 2-methoxydibenzosuberenone (compound 8) is dissolved in 30 ml of CH$_2$Cl$_2$. 1.24 g (2.2 eq.) of anhydrous AlCl$_3$ is added to the mixture, and the obtained mixture is refluxed for 24 hours. The reaction mixture is then poured into ice and water and then extracted with CH$_2$Cl$_2$. The extract is washed with saturated saline and dried over anhydrous MgSO$_4$, after which the solvent is evaporated, and the residue is purified by silica gel column chromatography (developing solvent: ethyl acetate-hexane=1:4) to give 0.685 g (yield 73%) of a product (compound 9) (melting point: 198° to 199° C., obtained by recrystallization from ethyl acetate-hexane).

| Elemental Analysis | | |
|---|---|---|
| | C | H |
| Theoretical ($C_{15}H_{10}O_2$) | 81.06 | 4.54 |
| Found | 80.81 | 4.35 |

NMR (CDCl$_3$) δ(ppm): 5.59 (1H, broad S, OH), 6.90–7.07 (4H, m, benzene ring $C_1$—H, $C_3$-H, aromatic H, $C_{10}$-H, $C_{11}$-H), 7.52–7.65 (3H, m, benzene ring $C_7$—H, $C_8$-H, $C_9$-H), 8.25 (1H, d, J=10.2 Hz, benzene ring $C_4$—H), 8.27 (1H, dd, J=1.8 Hz, J=9.1Hz, benzene ring $C_6$—H)

Ethyl-5-(dibenzo[a,d]cyclohepten-5-one-2-yl)oxyvalerate
(Compound 10)

1.62 g (7.3 mmol) of 2-hydroxydibenzosuberenone (compound 9) is dissolved in 15 ml of DMF. 0.321 g (1.1 eq.) of 60%-NaH is added to this mixture, and the resulting mixture is stirred at room temperature in N$_2$ atmosphere for 1 hour. While cooling with ice, 1.526 g (1 eq.) of ethyl-5-bromovalerate is added dropwise, and then the resulting mixture is stirred overnight at room temperature. The reaction mixture is poured into ice and water, neutralized with dilute hydrochloric acid, and then the obtained mixture is extracted with ethyl acetate. The extract is washed with saturated salines and the washed extract is dried over anhydrous MgSO$_4$, after which the solvent is evaporated, and the oily residue is purified by silica gel column chromatography (developing solvent: ethyl acetate-hexane, gradient ratio=1:7 to 1:2) to give 2.152 g (yield 84%) of a product (compound 10) (melting point 56° to 57° C., obtained by recrystallization from ethyl acetate-hexane).

| Elemental Analysis | | |
|---|---|---|
| | C | H |
| Theoretical ($C_{22}H_{22}O_4$) | 75.41 | 6.33 |
| Found | 75.37 | 6.34 |

NMR (CDCl$_3$) δ(ppm): 1.26 (3H, t, J=8.0 Hz, methyl), 1.8–1.9 (4H, m, ethylene —CH$_2$CH$_2$—), 2.40 (2H, t, J=8.0 Hz, methylene —CH$_2$O—), 4.01–4.18 (4H, m, methylene —CH$_2$COOEt, —COOCH$_2$—), 6.93 (1H, d, J=3.2 Hz, benzene ring $C_1$—H), 6.95 (1H, d, J=14 Hz, $C_{10}$-H), 7.04 (1H, d, J=14 Hz, $C_{11}$-H), 7.07 (1H, dd, J=3.0 Hz, J=10.5 Hz, benzene ring $C_3$—H), 7.5–7.64 (3H, m, benzene ring $C_7$—H, $C_8$-H, $C_9$-H), 8.25 (1H, d, J=10.2 Hz, benzene ring $C_4$—H), 8.28 (1H, dd, J=1.8 Hz, J=9.1 Hz, benzene ring $C_6$—H)

5-(dibenzo[a,d]cyclohepten-5-one-2-yl)oxyvalerianic Acid
(Compound 11)

1.7 g (4.86 mmol) of ethyl-5-(dibenzo[a,d]cyclohepten-5-one-2-yl)oxyvalerate (compound 10) is dissolved in 20 ml of dioxane. 10 ml of 2N NaOH solution is added to this mixture, and the obtained mixture is stirred at room temperature for 4 hours. The resulting mixture is acidified with diluted hydrochloric acid, and the solvent is evaporated under a reduced pressure to give 1.502 g (yield 96%) of a product (compound 11) (melting point: 123 to 124° C., obtained by recrystallization from ethyl acetate-hexane).

| Elemental Analysis | | |
|---|---|---|
| | C | H |
| Theoretical ($C_{20}H_{18}O_4$) | 74.52 | 5.63 |
| Found | 74.31 | 5.54 |

NMR (CDCl$_3$) δ(ppm): 1.8–1.95 (4H, m, ethylene), 2.46 (2H, t, J=7.7 Hz, methylene —CH$_2$O—), 4.09 (2H, t, J=6.7 Hz, methylene —CH$_2$COOH), 6.98 (1H, d, J=3.2 Hz, benzene ring $C_1$—H), 6.97 (1H, d, J=14 Hz, $C_{10}$-H), 7.04 (1H, d, J=14 Hz, $C_{11}$-H), 7.08 (1H, dd, J=3.2 Hz, J=10.5 Hz, benzene ring $C_3$—H), 7.5–7.64 (3H, m, benzene ring $C_7$—H, $C_8$-H, $C_9$-H), 8.24 (1H, d, J=10.5 Hz, benzene ring $C_4$—H), 8.28 (1H, dd, J=1.8 Hz, J=9.1 Hz, benzene ring $C_6$—H)

5,(5-Fmoc-aminodibenzo[a,d]cyclohepten-2-yl)oxyvalerianic Acid (Compound 12); (5-Fmoc-aminodibenzosuberenyl linker)

1.5 g (4.66 mmol) of 5-(dibenzo[a,d]-cyclohepten-5-one-2-yl)oxyvalerianic acid (compound 11) is dissolved in 80 ml of isopropyl alcohol, and 0.471 g (1 eq.) of triethylamine and 0.881 (5 eq.) of NaBH$_4$ is added to this mixture. The obtained mixture is stirred at 65° C. to 70° C. for 2 hours. The solvent is evaporated under a reduced pressure, and the residue is dissolved in H$_2$O. The mixture is acidified (pH=about 4.0) with glacial acetic acid while cooling with ice, and the resulting mixture is extracted with ethyl acetate. The extract is washed with saturated saline, and the washed extract is dried over anhydrous MgSO$_4$. After 2 ml of triethylamine is added to the mixture, the solvent is evaporated. The residue is dissolved in 20 ml of DMF, and 1.67 g (1.5 eq.) of Fmoc-NH$_2$ is added to the solution. 0,886 g (1 eq.) of p-toluene sulfonic acid is added to the resulting mixture, followed by stirring at room temperature for 1 hour. Water is added to the mixture while cooling with ice, the precipitating crystals are filtered. The crystals are washed with water and dried. The resulting crude product is purified by silica gel column chromatography (developing solvent: ethyl acetate-hexane (1:1), and then ethyl acetate (10% MeOH)) to give 2.112 g (yield 83%) of the product (compound 12) which is colorless crystals (melting point: 134° to 136° C., obtained by recrystallization from methanol).

| Elemental Analysis | | |
|---|---|---|
| | C | H |
| Theoretical ($C_{35}H_{31}O_5N$) | 77.04 | 5.73 |
| Found | 76.77 | 5.84 |

NMR (DMSO-d$_6$) δ(ppm): 1.59–1.80 (4H, m, ethylene), 2.28 (2H, t, J=7.7 Hz, methylene —CH$_2$O—), 3.97 (2H, t, J=7.0 Hz, methylene —CH$_2$COOH), 2.45 (3H, broad S, methylene, methine —CH$_2$CH<), 5.36 (1H, broad S, methine —C$_5$-H), 6.98–7.90 (17H, m, aromatic H), 8.4–8.8 (1H, broad S, NH), 12.0 (1H, broad S, —COOH)

Example 3

Introduction of 5-Fmoc-aminodibenzosuberyl Linker (Compound 7) and 5-Fmoc-aminodibenzosuberenyl Linker
(Compound 12) into Resin TENTAGEL S ™ (TGS-NH2))

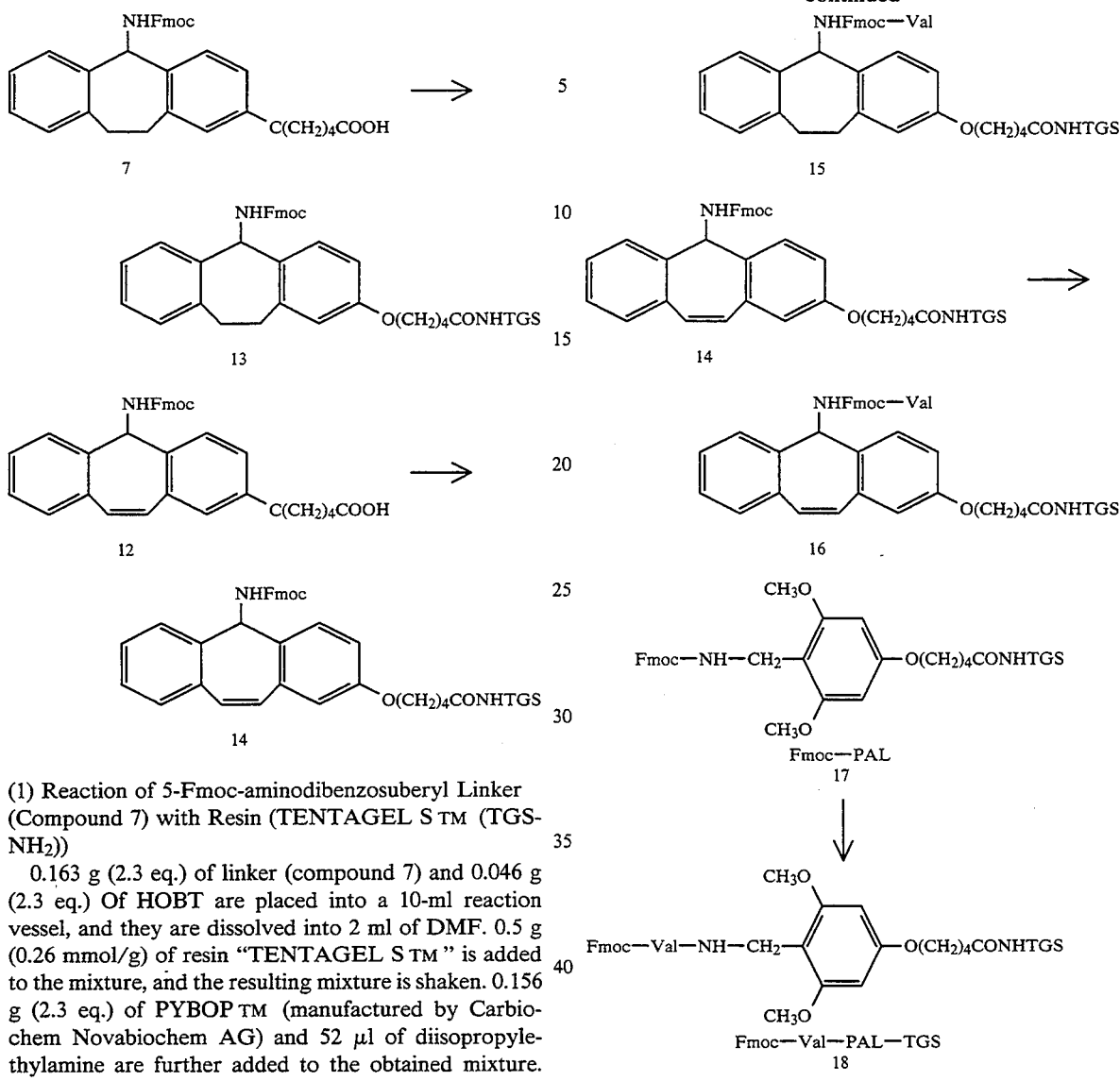

(1) Reaction of 5-Fmoc-aminodibenzosuberyl Linker (Compound 7) with Resin (TENTAGEL S ™ (TGS-NH₂))

0.163 g (2.3 eq.) of linker (compound 7) and 0.046 g (2.3 eq.) Of HOBT are placed into a 10-ml reaction vessel, and they are dissolved into 2 ml of DMF. 0.5 g (0.26 mmol/g) of resin "TENTAGEL S ™ " is added to the mixture, and the resulting mixture is shaken. 0.156 g (2.3 eq.) of PYBOP ™ (manufactured by Carbiochem Novabiochem AG) and 52 μl of diisopropylethylamine are further added to the obtained mixture. Thereafter, the reaction mixture is shaken at room temperature for 24 hours. The resin is filtrated, and then washed sequentially by DMF, CH₂Cl₂ and ether. The washed product is dried to yield a product (compound 13).

(2.) Reaction of 5-Fmoc-aminodibenzosuberenyl Linker (Compound 12) with Resin (TENTAGEL S ™ (TGS-NH₂))

The same procedures as in (1) above are carried out except that 0.163 9 (2.3 eq.) of linker (compound 12) is used to give a product (compound 14).

Example 4

Comparison of Cleavage Reaction Rates

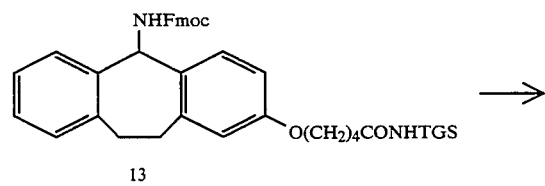

Valine is introduced into compounds 13 and 14, having linker compounds 7 and 12, respectively, introduced into a resin, to give compounds 15 and 16, respectively. Specifically, the linker (compounds 13 and 14)-resin is reacted with Fmoc-valine (10 eq.), HBOT (10 eq.), NMM (N-methylmorpholine) (15 eq.) and BOP (10 eq.) in a DMF solution for 90 minutes. The resin is collected by filtration, followed by washing with sequential additions of DMF, CH₂Cl₂ and MeOH, and the washed resin is dried to give compounds 15 and 16. The PAL ™ linker is used for comparison.

The Fmoc-Val-linker resin is added to a TFA/CH₂Cl₂ solution in 5% phenol, and the time course of the residual Fmoc-Val on the resin is quantitatively measured by UV spectrometry to determine the valine cleavage rate [M. S. Bernatowicz, S. B. Daniels and H. Koester, Tetrahedron Letters 30, 4645 (1989)].

The half-lives of valine cleaved from resin are as follows:

FmocVal-PAL ™ -TENTAGEL S ™ (18): about 12 minutes (50% CF₃COOH/CH₂Cl₂/5% phenol)

FmocVal-Linker (Compound 7)-TGS (15): about 3 minutes (50% CF₃COOH/CH₂Cl₂/5% phenol)

FmocVal-Linker (Compound 12)-TGS (16): about 3 minutes (10% CF₃COOH/CH₂Cl₂/5% phenol)

Example 5

Peptide Synthesis Using Novel Linkers (Compounds 7 and 12)

A substance K fragment (6 to 10 positions) and human secretin are respectively synthesized using the linker (compound 7)-TGS and the linker (compound 12)-TGS. The peptide synthesizer used is "Simultaneous Peptide Synthesizer, Shimadzu Model PSSM-8 ™ (manufactured by Shimadzu Corporation)" (K. Nokihara et al., Peptide Chemistry 1991, ed., A. Suzuki, Protein Research Foundation, Osaka 1992, pp. 203–208).

1) Substance K Fragment (6 to 10 positions)

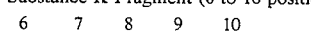

6   7    8    9    10
Phe—Val—Gly—Leu—Met—NH₂

(SEQ. ID. NO. 1)

2) Human Secretine Consisting of 27 Amino Acids 27  26  25  24  23  22  21  20  19  18
His—Ser—Asp—Gly—Thr—Phe—Thr—Ser—Glu—Leu—
17  16  15  14  13  12  11  10  9   8
Ser—Arg—Leu—Arg—Glu—Gly—Ala—Arg—Leu—Gln—
7   6   5   4   3   2   1
Arg—Leu—Leu—Gln—Gly—Leu—Val—NH₂

(SEQ. ID. NO. 2)

The peptide of 1) and 2) are synthesized by the HBTU method using the peptide synthesizer PSSM-8 ™. Each amino acid is previously dissolved in DMF and dispensed to the amino acid station. The resins used are 30 mg of the linker (compound 7)-TENTAGEL S ™ and 30 mg of the linker (compound 12)-TENTAGEL S ™, both synthesized by the methods described above.

Schematic Flowchart for Synthesis Using PSSM

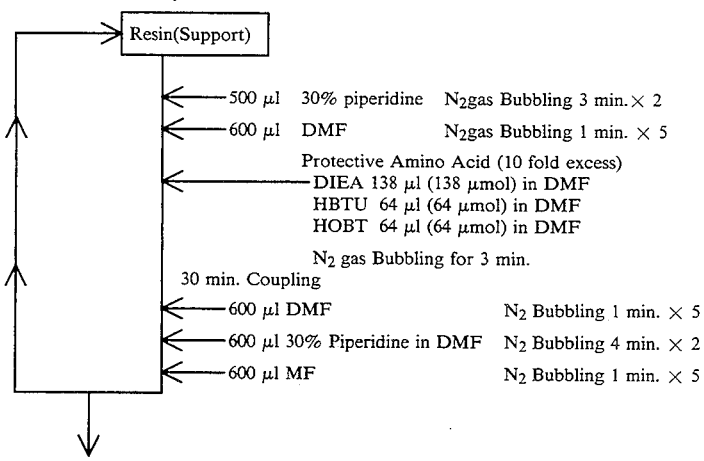

Incorporation of the N-Terminal Amino Acid
   Washing with Methanol
   Washing with t-Butyl ethyl ether Drying Cleavage takes place by adding 0.3 to 0.5 ml of a cleavage cocktail comprising 82% TFA, 3% ethyl methyl sulfide, 5% H₂O, 5% thioanisole, and 2% thiophenol to 30 mg of each resin, and keeping the mixture standing at room temperature for 7 hours. The solution alone is taken out from the reaction vessel by means of bubbling N₂ gas. Anhydrous ether is added to the solution to give a precipitate. After the resulting precipitate is purified by HPLC, the resulting peptides 1) and 2) are subjected to liquid secondary ion mass spectrometry to identify their molecular mass and sequence by the use of protein sequencer. These peptides are verified to be identical to separately synthesized respective authentic samples by a reverse-phase HPLC.

The basic cycle in automated peptide synthesis is shown below. The independent 8-channel synthesis system permits synthesis of high purity peptides because no cross contamination (mutual contamination between channels) takes place. Also, the amount of synthesis can be adjusted for each channel (0.005 to 0.4 mmol/run). With these features, the present system serves as an efficient peptide synthesizer capable of simultaneously producing eight different peptides at high purity in desired amounts.

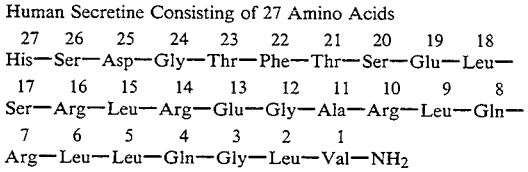

1. Standard Cycle: → Piperidine → Acylation →

2. Final Cycle: Piperidine → Acylation →
   Piperidine → Reaction Terminated ( → : Washing)

| Step | Procedure | Time (× Number of Runs) |
|---|---|---|
| | Standard Cycle | |
| 1 | Washing with DMF | 1 min. × 1 |
| 2 | Washing with Piperidine in 30% DMF | 5 min. × 1 |
| 3 | | 3 min. × 1 |
| 4 | Washing with DMF | 1 min. × 5 |
| 5 | Activation of Amino Acid | 1 to 3 min. |
| 6 | Coupling (Resin Mixing) | 30 min. |
| 7 | Washing with DMF | 1 min. × 4 |
| | Final Cycle | |
| 100 | Washing with DMF | 1 min. × 1 |
| 101 | Washing with Piperidine | 5 min. × 1 |
| 102 | | 3 min. × 1 |
| 103 | Washing with DMF | 1 min. × 5 |
| 104 | Washing with Methanol | 1 min. × 2 |
| 105 | Washing with t-Butyl ethyl ether | 0.5 min. × 1 |

| | |
|---|---|
| 106 N₂ Blowing | 10 min. |

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A compound represented by the following formula (I):

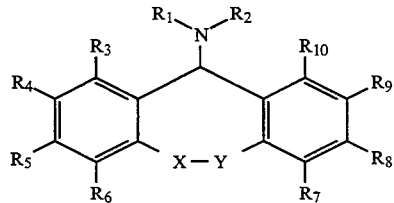

wherein $R_1$ represents a hydrogen atom, an amino acid residue protected by an amino-protecting group which is removable in the presence of a base, or an α-fluorenylmethyloxycarbonyl group; $R_2$ represents a hydrogen atom or an alkyl group having 1 to 4 carbon atoms; one substituent selected from the group consisting of $R_3$, $R_4$, $R_5$, $R_6$, $R_7$, $R_8$, $R_9$ and $R_{10}$ represents —O—$(CH_2)_n$—COOH, wherein n is an integer of 1 to 6, and all of the remaining substituents independently represent a hydrogen atom, an alkyl group having 1 to 4 carbon atoms, or an alkoxy group having 1 to 4 carbon atoms; and —X—Y— represents a —C—C—bond or a —C≡C— bond.

2. The compound according to claim 1, wherein $R_1$ represents an amino acid residue protected by an α-fluorenylmethyloxycarbonyl group, or an α-fluorenylmethyloxycarbonyl group, and $R_2$ represents a hydrogen atom.

3. The Compound according to claim 1 or 2, wherein said one substituent selected from the group consisting of $R_3$, $R_4$, $R_5$, $R_6$, $R_7$, $R_8$, $R_9$ and $R_{10}$ represents —O—$(CH_2)_4$—COOH.

4. The compound according to claim 3, wherein at least four substituents selected from the group consisting of $R_3$, $R_4$, $R_5$, $R_6$, $R_7$, $R_8$, $R_9$ and $R_{10}$ are hydrogen atoms.

5. The compound according to claim 1, which is 5-(5-Fmoc-amino-10,11-dihydrodibenzo[a,d]cyclohepten-2-yl)oxyvalerianic acid.

6. The compound according to claim 1, which is 5-(5-Fmoc-aminodibenzo[a,d]cyclohepten-2-yl) oxyvalerianic acid.

7. A peptide amide linker for peptide synthesis, comprising a compound as recited in claim 1.

* * * * *